United States Patent [19]

Asinger et al.

[11] 4,045,479
[45] Aug. 30, 1977

[54] PROCESS OF PREPARING PENICILLAMINE

[75] Inventors: Friedrich Asinger, Rott; Heribert Offermanns, Grossauheim; Karl-Heinz Gulzek, Alpen, all of Germany

[73] Assignee: Deutsche Gold- und Silber-Scheideanstalt vormals Roessler, Frankfurt, Germany

[21] Appl. No.: 598,995

[22] Filed: July 25, 1975

Related U.S. Application Data

[63] Continuation of Ser. No. 306,370, Nov. 14, 1972, abandoned, which is a continuation-in-part of Ser. No. 158,512, June 30, 1971, abandoned.

[30] Foreign Application Priority Data

| July 3, 1970 | Germany | 2032952 |
| May 11, 1971 | Germany | 2123232 |
| Nov. 15, 1971 | Germany | 2156601 |

[51] Int. Cl.² .............................................. C07C 99/00
[52] U.S. Cl. .......................... 260/534 S; 260/306.7 C
[58] Field of Search ................................... 260/534 S

[56] References Cited

FOREIGN PATENT DOCUMENTS

738,520  9/1969  Belgium .......................... 260/534 S

OTHER PUBLICATIONS

Wagner et al., "Synthetic Organic Chemistry," (1953), pp. 412, 413, 570.

*Primary Examiner*—Joseph E. Evans
*Attorney, Agent, or Firm*—Cushman, Darby & Cushman

[57] ABSTRACT

Penicillamine or a homolog thereof is made by reacting an aldehyde branched at the α-carbon atom, sulfur and ammonia to form a thiazoline- $\Delta^3$; converting the latter compound by reaction with anhydrous hydrogen cyanide into the corresponding thiazolidine-4-carbonitrile; hydrolyzing the nitrile with an aqueous concentrated hydrochloric acid containing at least 30% by weight of hydrogen chloride at a temperature between 40° and 70° C to form the hydrochloric salt of the thiazolidine-4-acid amide and then, at a higher temperature continuing the hydrolysis to form the salt of the thiazolidine-4-carboxylic acid together with the ammonium salt. The ammonium salt is then separated from the mixture and the carboxylic acid hydrochloride is hydrolytically decomposed whereby the penicillamine is obtained.

8 Claims, No Drawings

PROCESS OF PREPARING PENICILLAMINE

CROSS-REFERENCE TO RELATED APPLICATIONS

The present application is a continuation of application Ser. No. 306,370, filed Nov. 14, 1972, which in turn is a continuation-in-part of application Ser. No. 158,512 filed by the same inventors now June 30, 1971, both of which are now abandoned.

BACKGROUND OF THE INVENTION

It is known to obtain penicillamine by reaction of isobutyraldehyde with sulfur and ammonia and converting the thus obtained thiazoline-$\Delta^3$ by reaction with hydrogen cyanide to the corresponding thiazolidine-4-carbonitrile. The nitrile is then hydrolyzed by reaction with mineral acids. It is thus obtained, first, thiazolidine-4-acid amide and then thiazolidine-4-carboxylic acid and the ammonium salt. The ammonium salt is separated and the carboxylic acid is hydrolytically decomposed and thus converted into the penicillamine hydrochloride.

The present process is an improvement over the process of the above second noted U.S. application where the hydrolysis was carried out in two stages. In the first stage the reaction was effected at low temperature. In the second stage of the hydrolysis a higher temperature was then employed.

SUMMARY OF THE INVENTION

The present invention resides in the finding that better results can be obtained if the hydrolysis in the first stage where the nitrile is converted to the acid amide is carried out at a temperature between about 40° and 70° C in an aqueous hydrochloric acid containing at least 30% by weight of hydrogen chloride, the amount of hydrogen chloride preferably being between about 1500 and 3000 ml of acid per mol of nitrile.

DESCRIPTION OF THE DETAILS OF THE INVENTION AND OF PREFERRED EMBODIMENTS

The hydrogen cyanide which is used for converting the thiazolines to the thiazolidine-4-carbonitriles can be used in gaseous or liquid form or may be formed in situ by the action of mineral acids such as concentrated sulfuric acid upon cyanides. The reaction mass can be formed without using solvents or in the presence of organic solvents particularly alkanols such as methanol, ethers such as diethylether, aliphatic hydrocarbons or aromatic hydrocarbons such as low boiling point gasoline or halogenated hydrocarbons such as tetrachloromethane.

The nitriles which are formed in the reaction may be separated from the reaction mass and then subjected to the hydrolysis. However the reaction mass can also be directly employed for the hydrolysis reaction. The latter process is particularly useful where the formation of the nitriles is effected in the absence of organic solvents. As is mentioned in the above second noted U.S. application the hydrolysis of the nitriles may be effected in an aqueous medium, that is in the absence of organic solvents. The first stage of the hydrolysis as is mentioned in the listed U.S. application may be employed at room temperature using a minimum of about 200 ml and preferably between about 400 and 1000 ml of concentrated aqueous hydrochloric acid per mol of nitrile.

It has now been found that the hydrolysis of the nitriles in the aqueous medium should be effected in the first stage at a temperature between about 40° and 70° C and preferably between 50° and 60° C. It is preferred to mix the acid with the nitrile at a temperature of about 20° to 30° C and then to increase the temperature slowly to a range between about 40° and 70° C.

The nitriles or the reaction mass obtained in forming the nitriles is preferably introduced for the purpose of the hydrolysis into the aqueous hydrochloric acid which should contain 35 to 38% by weight and in any case at least about 30% by weight of hydrogen chloride. Preferably at least about 1000 ml and most preferably between about 1500 and 3000 ml of hydrochloric acid are used per mol of nitrile.

To effect the hydrolysis the nitriles are maintained in the hydrochloric acid for about 6 to 15 hours at temperatures between about 40° and 70° C. Preferably air is excluded during the reaction. The temperatures should usually be in the lower portion of the temperature range if the reaction time is between about 10 and 15 hours while a temperature in the upper range should be used in case of a reaction time between about 6 and 8 hours. The reaction time can further be shortened by employing an elevated pressure.

The thiazolidine-4-acid amide hydrochloride is then separated from the reaction mass in conventional manner. The acid amide hydrochloride is then taken up in aqueous mineral acid and is further heated to temperatures between about 80° and 150° C as described in the above earlier U.S. application in order to obtain the thiazolidine-4-carboxylic acids. In this stage of the reaction preferably an aqueous hydrochloric acid is employed which has about 10 to 15% by weight content of hydrogen chloride. The amount preferably is about 300 ml per mol of acid amide.

If an aqueous hydrochloric acid is used to convert the nitriles into the acid amides it is preferred to further heat the acid amides directly within the reaction mass obtained in the previous case. It is not necessary in this case that the nitriles are completely converted to the acid amides. The reaction mass preferably is heated to boiling point and if desired a slightly elevated pressure of for instance 3 to 6 atm. may be used.

The reaction mass obtained in the hydrolysis contains the thiazolidine-4-carboxylic acids as salts of the mineral acid together with ammonium salts. In order to further process this mixture, to convert the thiazolidine-4-carboxylic acid salt into the penicillamine or its homologs and to separate the ammonium salt the further procedure is as usual, especially follows the process described in the above earlier application.

The following examples will further illustrate the invention:

The concentrated hydrochloric acid used in these examples is an acid containing about 37% by weight of hydrogen chloride.

EXAMPLE 1

Gaseous ammonia was introduced into a mixture of 1442 g (20 mol) of freshly distilled isobutyraldehyde which did not contain any isobutyraldehyde trimers, 101 g (1 mol) of triethylamine and 320 g (10 mol) of sulfur. The mixture was maintained at boiling point during the introduction of the gas and was dehydrated azeotropically. The reaction took place in 7 hours. During this period 400 ml of water were eliminated. By distillation at a reduced pressure of 20 torr 1247 g of 2-isopropyl-5,5-dimethyl-thiazoline-Δ³ corresponding to 79% yield were obtained.

157 g (1 mol) of the latter compound were then reacted with 45 ml (1.2 mol) of hydrogen cyanide dropwise and while stirring. The temperature was maintained at 5° to 10° C. The mixture successively was stirred for 1 hr. at 5° to 10° C and for 3 hours at 20° to 25° C.

The reaction mass then contained 2-isopropyl-5,5-dimethyl-thiazolidine-4-carbonitrile. This mass was introduced into 1500 ml of concentrated hydrochloric acid which was at a temperature of 20° C. The mixture was maintained for 15 hours while stirring at a temperature of 40° to 45° C. In a specimen run it was determined that a yield had thus been obtained of 76% of 2-isopropyl-5,5-dimethyl-thiazolidine-4-acid amide-hydrochloride relative to the initial 2-isopropyl-5,5-dimethyl-thiazoline-Δ³. For the purpose of the present example however the reaction mass obtained in the first hydrolysis stage at the temperature of 40° to 45° C was then directly further heated to boiling point, and was maintained for 8 hours under reflux at this temperature whereupon it was evaporated to dryness at a reduced pressure. The residue comprised the 2-isopropyl-5,5-dimethyl-thiazolidine-4-carboxylic acid hydrochloric plus ammonium chloride. The carboxylic acid hydrochloride was extracted from the reaction mass with methanol. The methanol was then evaporated and the residue was washed with acetone. There were thus obtained 209.5 g of 2-isopropyl-5,5-dimethyl-thiazolidine-4-carboxylic acid hydrochloric corresponding to a yield of 87.5% relative to the initial 2-isopropyl-5,5-dimethyl-thiazoline-Δ³.

The product was of uniform composition as could be determined by thin layer chromatography. It had a melting point of 210° to 212° C with decomposition.

EXAMPLE 2

The same process was used as in Example 1. However, the mixture containing the 2-isopropyl-5,5-dimethyl-thiazolidine-4-carbonitrile was maintained for 6 hours while stirring at 65° to 70° C in the mixture with 1500 ml of concentrated aqueous hydrogen chloride. There were obtained 187 g of 2-isopropyl-5,5-dimethyl-thiazolidine-4-carboxylic acid hydrochloride corresponding to the yield of 78.2% relative to the initial 2-isopropyl-5,5-dimethyl-thiazoline-Δ³. The product had the same purity as that obtained in the process of Example 1.

EXAMPLE 3

The same process was used as in Example 1. However the reaction mass containing the 2-isopropyl-5,5-dimethyl-thiazolidine-4-carbonitrile was introduced into 3000 ml concentrated aqueous hydrogen chloride. The reaction mass was maintained for 15 hours, while stirring, at a temperature of 40° to 45° C. It was then evaporated to dryness at a reduced pressure. The residue was washed with acetone. There were obtained 210 g of 2-isopropyl-5,5dimethyl-thiazolidine-4-acid amide-hydrochloride corresponding to a yield of 87.8% relative to the initial 2-isopropyl-5,5-dimethyl-thiazolidine-Δ³.

The acid amide hydrochloride contained small amounts of 2-isopropyl-5,5-dimethyl-thiazolidine-4-carboxylic acid hydrochloride. It had a melting point of 238° to 240° C with decomposition.

In order further to convert the entire mass to the carboxylic acid hydrochloride the reaction mass was dissolved in a mixture of 100 ml water and 300 ml of concentrated aqueous hydrochloric acid. The solution was maintained for 8 hours at boiling point under reflux. The final yield of 2-isopropyl-5,5-dimethyl-thiazolidine-4-carboxylic acid hydrochloride was 99% relative to the initial 2-isopropyl-5,5-dimethyl-thiazolidine-4-acid amide hydrochloride.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

1. In a process of preparing penicillamine or a homologue thereof by reacting together an aldehyde branched at the α-carbon atom, sulfur, and ammonia to form a thiazoline-Δ³, converting the thiazoline-Δ³ by reaction with anhydrous hydrogen cyanide to the corresponding thiazolidine-4-carbonitrile, hydrolyzing the carbonitrile with hydrochloric acid to form first the hydrochloride of the corresponding thiazolidine-4-carboxamide and then, at a higher temperature, to form the hydrochloride of the thiazolidine-4-carboxylic acid and an ammonium salt, separating the ammonium salt from the mixture and decomposing the thiazolidine-4-carboxylic acid hydrochloride by hydrolysis to form penicillamine or a homologue thereof, the improvement which consists essentially of the step of hydrolyzing the carbonitrile to the carboxamide by heating at a temperature between about 40° and 70° C a mixture of the carbonitrile and at least the amount of aqueous hydrochloric acid containing at least 30% by weight of hydrogen chloride that is required stoichiometrically to form the corresponding thiazolidine-4-carboxamide hydrochloride.

2. A process as defined in claim 1 in which the carbonitrile is 2-isopropyl-5,5-dimethylthiazolidine-4-carbonitrile.

3. A process as defined in claim 1 in which the amount of hydrochloric acid is between about 1500 and 3000 milliliters per mol of carbonitrile.

4. A process as defined in claim 1 in which the mixture is heated at a temperature between 50° and 60° C.

5. A process as defined in claim 1 in which the carbonitrile and hydrochloric acid are mixed together at a temperature between about 20° and 30° C and are then gradually heated to a temperature between about 40° and 70° C and the heating is continued at a temperature within the range between about 40° and 70° C.

6. A process as defined in claim 1 in which the hydrochloric acid contains between 35 and 38% by weight of hydrogen chloride.

7. A process as defined in claim 1 in which the heating is conducted in the absence of air.

8. A process as defined in claim 1 in which the mixture containing the carboxamide hydrochloride that is produced in said process is then heated at a temperature between about 80° and 150° C to convert the carboxamide contained therein to the corresponding carboxylic acid.

* * * * *